(12) United States Patent
Pozzato et al.

(10) Patent No.: US 11,679,909 B2
(45) Date of Patent: Jun. 20, 2023

(54) COLLAPSIBLE AND ASSEMBLABLE CONTAINER

(71) Applicants: Francesco Pozzato, Hong Kong (HK);
Frederic Gooris, Hong Kong (HK);
Chen Ying Paulina Chu, Hong Kong (HK)

(72) Inventors: Francesco Pozzato, Hong Kong (HK);
Frederic Gooris, Hong Kong (HK);
Chen Ying Paulina Chu, Hong Kong (HK)

( * ) Notice: Subject to any disclaimer, the term of this patent is extended or adjusted under 35 U.S.C. 154(b) by 313 days.

(21) Appl. No.: 17/182,163

(22) Filed: Feb. 22, 2021

(65) Prior Publication Data
US 2022/0135280 A1 May 5, 2022

Related U.S. Application Data

(60) Provisional application No. 63/107,457, filed on Oct. 30, 2020.

(51) Int. Cl.
*B65D 21/08* (2006.01)
*A61L 2/26* (2006.01)
*A61L 2/10* (2006.01)

(52) U.S. Cl.
CPC .............. *B65D 21/086* (2013.01); *A61L 2/10* (2013.01); *A61L 2/26* (2013.01); *A61L 2202/11* (2013.01);
(Continued)

(58) Field of Classification Search
CPC . B65D 21/086; A61L 2/10; A61L 2/26; A61L 2202/11; A61L 2202/121; A61L 2202/122; A61L 2202/14; A61L 2202/16
(Continued)

(56) References Cited

U.S. PATENT DOCUMENTS

| 5,902,552 A | * | 5/1999 | Brickley | .................. A61L 2/10 |
| | | | | 362/267 |
| 2004/0051056 A1 | * | 3/2004 | Disabito | ................. A61L 9/015 |
| | | | | 250/504 R |

(Continued)

FOREIGN PATENT DOCUMENTS

| CN | 205906358 U | 1/2017 |
| CN | 209080422 U | 7/2019 |
| CN | 211593265 U | 9/2020 |

OTHER PUBLICATIONS

International Search Report and Written Opinion of corresponding PCT Patent Application No. PCT/CN2021/112078 dated Nov. 12, 2021.

*Primary Examiner* — Nicole M Ippolito
(74) *Attorney, Agent, or Firm* — Idea Intellectual Limited; Margaret A. Burke; Sam T. Yip (57) ABSTRACT

A collapsible and assemblable container for sterilization, including but not limited to UV sterilization, of objected placed in the container. The container includes moveable panels with an electronic circuit board including one or more actuating elements such as UV LEDs. The electronic circuit board further includes sensors that prohibit the actuating elements from being activated unless the collapsible container is fully and correctly deployed, preventing any harmful exposure to the actuating elements that can lead to eye damage, skin cancer, etc. to the user. The electronic circuit board cooperates with switch elements that activate the actuating elements only when the collapsible container is fully and correctly deployed.

18 Claims, 9 Drawing Sheets

(52) U.S. Cl.
CPC ... *A61L 2202/121* (2013.01); *A61L 2202/122* (2013.01); *A61L 2202/14* (2013.01); *A61L 2202/16* (2013.01)

(58) Field of Classification Search
USPC .......................... 250/453.11, 454.11, 455.11
See application file for complete search history.

(56) References Cited

U.S. PATENT DOCUMENTS

| | | |
|---|---|---|
| 2015/0175295 A1 | 6/2015 | Chalifoux |
| 2019/0112094 A1 | 4/2019 | Dwork |
| 2022/0096676 A1* | 3/2022 | McCanless ............... A61L 2/24 |

\* cited by examiner

COLLAPSIBLE AND ASSEMBLABLE CONTAINER

CROSS REFERENCE TO RELATED APPLICATION

The present application claims priority from U.S. provisional patent application Ser. No. 63/107,457 filed Oct. 30, 2020, the disclosure of which is incorporated herein by reference in its entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention generally relates to a collapsible and assemblable container which may be used for sterilization or other functions and having an actuating element cooperating with two or more switches such that the switches are only closed and the actuating elements may only be operated when the box is fully assembled, ensuring operating safety.

BACKGROUND

In the container industry, there are a number of known applications for collapsible containers. However, most collapsible containers have multiple moveable panels that may be deployed incorrectly or only partially, resulting in the incomplete formation of the required enclosed container. When performing UV sterilization, if a container is improperly formed, harmful UV radiation may be emitted that can result in eye damage, skin cancer, etc.

In addition, once the container is folded into a deployed configuration, users are often required to apply tape, another adhesive, or other mechanical fixation in order to hold the container in the deployed configuration. Therefore, in view of the shortcomings of the existing collapsible containers, there is a need in the art to provide a collapsible container with extremely high safety.

SUMMARY OF THE INVENTION

To address the above-mentioned shortcomings, the present invention provides a collapsible and assemblable container that addresses the problems of poor portability, improper formation, and safety of traditional collapsible containers. The collapsible container of the present invention is lightweight and easily folds flat into a compact form for storage and transport.

In accordance to one aspect, the present invention provides a collapsible and assemblable container, including a first moveable panel with a first sensor element; a second moveable panel with an electronic circuit board, which includes one or more actuating elements cooperating with at least three interlock switch elements, and the at least three interlock switch elements control the one or more actuating elements; a third moveable panel partially with a second sensor element; and a fourth moveable panel with a third sensor element. During container assembly, the third moveable panel and the fourth moveable panel form an inner enclosure portion, the first moveable panel and the second moveable panel are configured as upper covers of the container, and the first moveable panel is positioned on top of the second moveable panel. The second sensor element of the third moveable panel interacts with a first of the at least three interlock switch elements, and the third sensor element of the fourth moveable panel interacts with a second of the at least three interlock switch elements. If the first sensor element of the first moveable panel does not interact with a third of the at least three interlock switch elements, the electronic circuit board remains OFF. Otherwise, if the first sensor element of the first moveable panel interacts with a third of the at least three interlock switch elements, the one or more actuating elements are actuated.

In one embodiment, the one or more actuating elements include sterilization elements, heating elements, spray elements, or laser elements.

In another embodiment, the sterilization elements include at least three UV LEDs.

In one embodiment, the at least three interlock switch elements include reed switches, magnetic-activated switches, optical sensor-activated switches, mechanical-activated switches, or temperature-activated switches. It should be noted that the present invention does not exclude the use of fewer interlock switch elements, such as only one interlock switch element, or two interlock switch elements.

In one embodiment, the electronic circuit board further includes a power element comprising a rechargeable battery and a connector.

In another embodiment, the connector includes a USB port or a Type-C port.

In one embodiment, all panels are made from insulating materials or waterproof materials.

In one embodiment, the insulating materials includes one or more of glass fibers, silicone, polytetrafluoroethylene (PTFE), carbon fibers, aluminum and stainless steel.

In one embodiment, the waterproof materials include one or more of polytetrafluoroethylene (PTFE), glass fibers, silicone, polyurethane (PU), aluminum, stainless steel and polycarbonate.

In one embodiment, the sensor elements are magnets, and the magnets are attracted to mating magnets on adjacent panels when the container is fully formed; alternatively, mechanical fasteners may be employed such as snaps, hook and loop fasteners such as VELCRO, zippers, ties, or other fasteners.

In one embodiment, the electronic circuit board further includes one or more sensors that prohibit the one or more actuating elements from being activated unless the collapsible container is fully and correctly deployed.

In one embodiment, the first and second panels are connected by plural intermediate panels.

In another embodiment, the third and fourth panels are positioned over the plural intermediate panels.

In yet another embodiment, the plural intermediate panels form an outer enclosure portion surrounding the inner enclosure portion formed by the third and fourth panels.

BRIEF DESCRIPTION ON THE DRAWINGS

Embodiments of the invention are described in more detail hereinafter with reference to the drawings, in which.

DETAILED DESCRIPTION OF THE INVENTION

In the following description, depictions of collapsible and assemblable containers are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

The present invention solves the problem of radiation leakage from incompletely formed containers. In one aspect, the invention uses an electronic circuit board that includes one or more actuating elements, such as UV LEDs, cooperating with at least three interlock switch elements. This permits the actuating elements to be activated only when the formed container is properly closed.

The collapsible and assemblable container adopts an innovative folding process and can be assembled into a box or flattened into a planar shape for storage at any time. Foldable containers provide benefits over non-foldable containers at least because foldable containers can be folded from a flat configuration into a three-dimensional configuration.

The embodiments of the collapsible and assemblable container of the present invention will be described below with reference to FIGS. 1-8.

Figure 1:
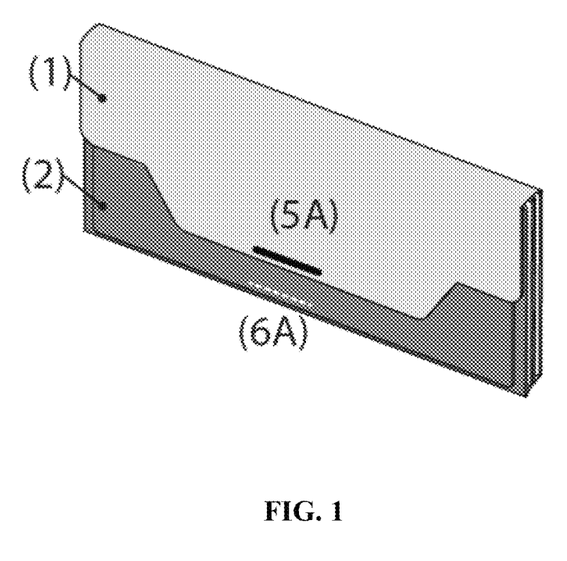
FIG. 1 depicts an isometric view of the collapsible container in the smallest and most compact stage.
Figure 3:
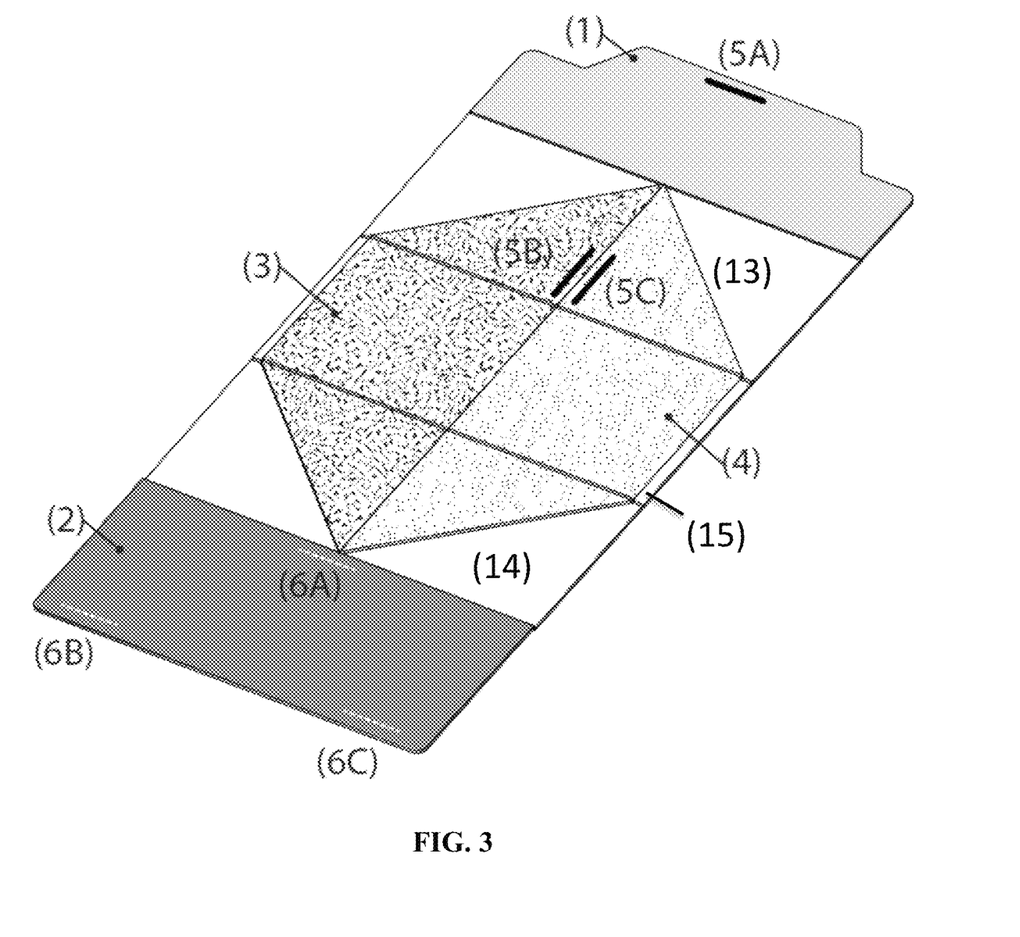
FIG. 3 depicts an isometric view of the collapsible container completely flat.

Turning to FIG. 1, the container includes a first moveable panel 1 and a second moveable panel 2. As best seen in FIG. 5, moveable panels 1 and 2 will assemble as covering portions of an enclosure that are assembled from collapsible panels 3 and 4. FIG. 3 depicts the third moveable panel 3; and a fourth moveable panel 4. The third and fourth moveable panels 3 and 4 assemble into an enclosure portion, best seen in FIG. 4. Each of collapsible panels 3 and 4 include approximately rectangular and triangular sections, with the rectangular sections forming enclosure ends and the triangular sections assembling together to form enclosure sides as seen in FIGS. 4 and 5.

As seen in FIG. 3, the foldable container has been opened from a first folded configuration of FIG. 1 to an approximately flat, open structure. The foldable container includes two major folding sub-assemblies. The first subassembly is comprised of moveable panels 1 and 2 which are interconnected through plural intermediate panels 13, 14, and 15. Third and fourth moveable panels 3 and 4 are positioned on plural intermediate panels 13, 14, and 15, with each of the panels 3 and 4 including the two triangular sections interconnected by a rectangular section. The user opens moveable panels 3 and 4, which assemble to forms an inner enclosure portion, best seen in FIG. 4. In the assembled container configuration of FIG. 5, foldable sections 13, 14, and 15 surround the inner enclosure portion assembled from the third and fourth moveable panels 3 and 4.

The first moveable panel 1 includes a first sensor element 5A, while the second moveable panel 2 includes interlock switch elements 6A, 6B, 6C. As used herein, the term "interlock" or "interlock switch" is used to broadly denote any mechanical, electrical, magnetic, or electromagnet element the cooperates with another element to prevent or permit operation of the actuating element (e.g., sterilizing element such as UV LEDs) in the present invention. In some cases, the interlock cooperates with a sensor, in other embodiments, the interlock may be any commercially-available two-part interlock that, when the two parts are separated, the switch is in an open state and when the two parts are together is in a closed state, permitting operation of the actuating element. The third moveable panel 3 includes a second sensor element 5B. The third moveable panel 3 includes sensor element 5B while the fourth moveable panel 4 includes a third sensor element 5C.

Figure 4:
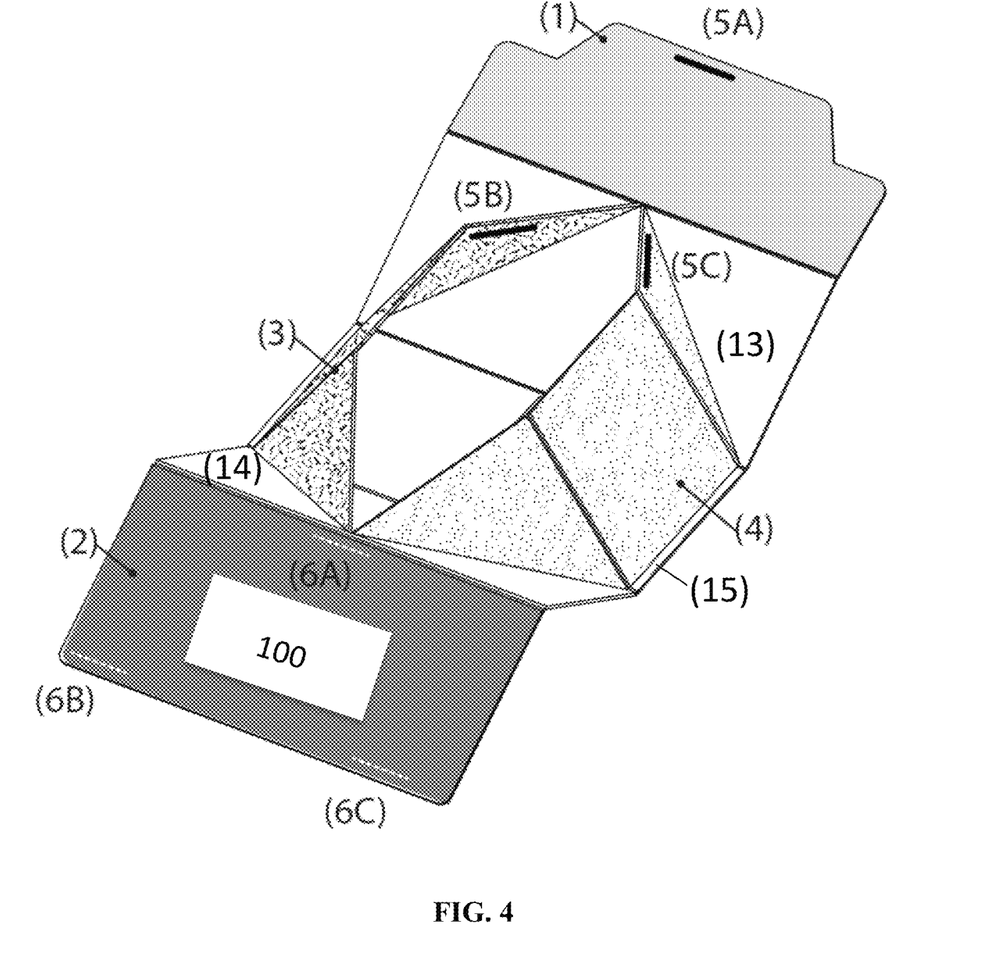
FIG. 4 depicts an isometric view of the collapsible container that start to approach the box stage.
Figure 5:
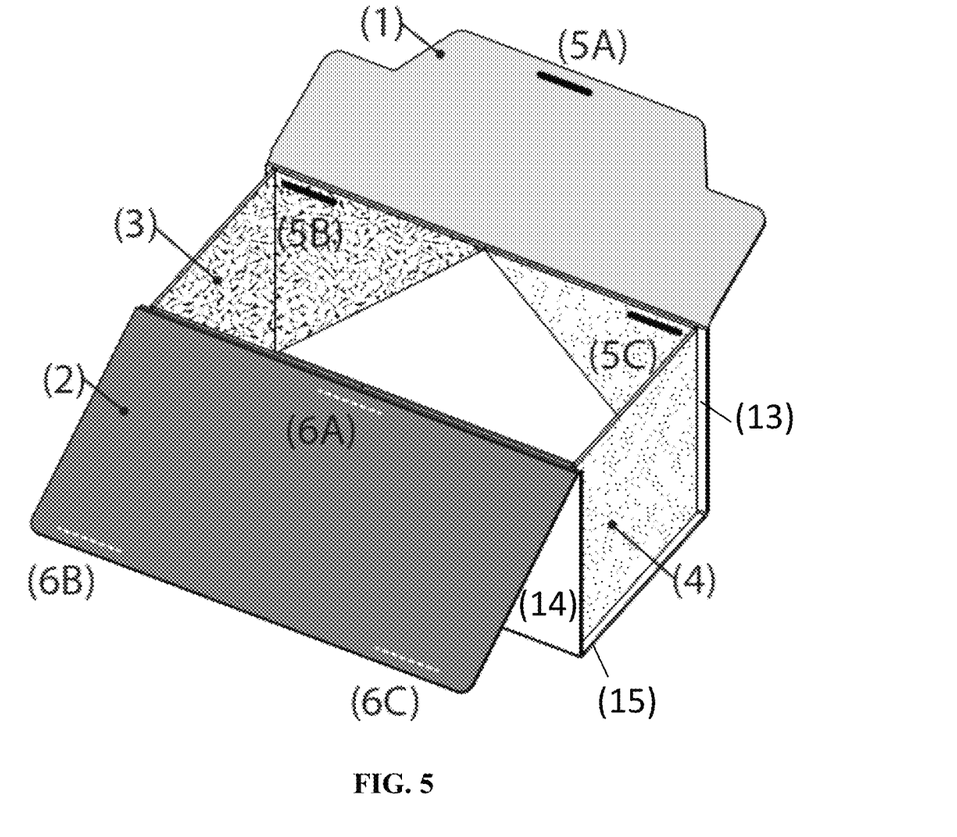
FIG. 5 depicts an isometric view of the collapsible container that formed as box but open on the top.

In one embodiment, the second moveable panel 2 includes an electronic circuit board 100, at the position indicated in FIG. 4. The circuit board 100 is shown schematically in FIG. 8, which includes one or more actuating elements such as UV LEDs that cooperate with interlock switch elements 6A, 6B, 6C. The interlock switch elements 6A, 6B, 6C may cooperate with the electronic circuit board 100 through a wired or wireless connection and are responsible for controlling the one or more actuating elements. When a fully-assembled container is formed, the second sensor element 5B of the third moveable panel 3 interacts with a first of the at least three interlock switch elements 6B, and the third sensor element 5C of the fourth moveable panel 4 interacts with a second of the at least three interlock switch elements 6C.

In one case, if the first sensor element 5A of the first moveable panel 1 does not interact with a third of the at least three interlock switch elements 6A, the electronic circuit board 100 remains OFF.

In another case, if the first sensor element 5A of the first moveable panel 1 interacts with a third of the at least three interlock switch elements 6C, the one or more actuating elements are actuated.

Referring to FIG. 1, when the collapsible container is folded, the sensor elements 5A, 5B, 5C will not interact with interlock switch elements 6A, 6B, 6C connected to the electronic circuit board integrated in the second moveable panel 2. Therefore, the electronic circuit board 100 cannot be engaged and remains OFF. The folded container is portable and takes up less space.

Figure 2:
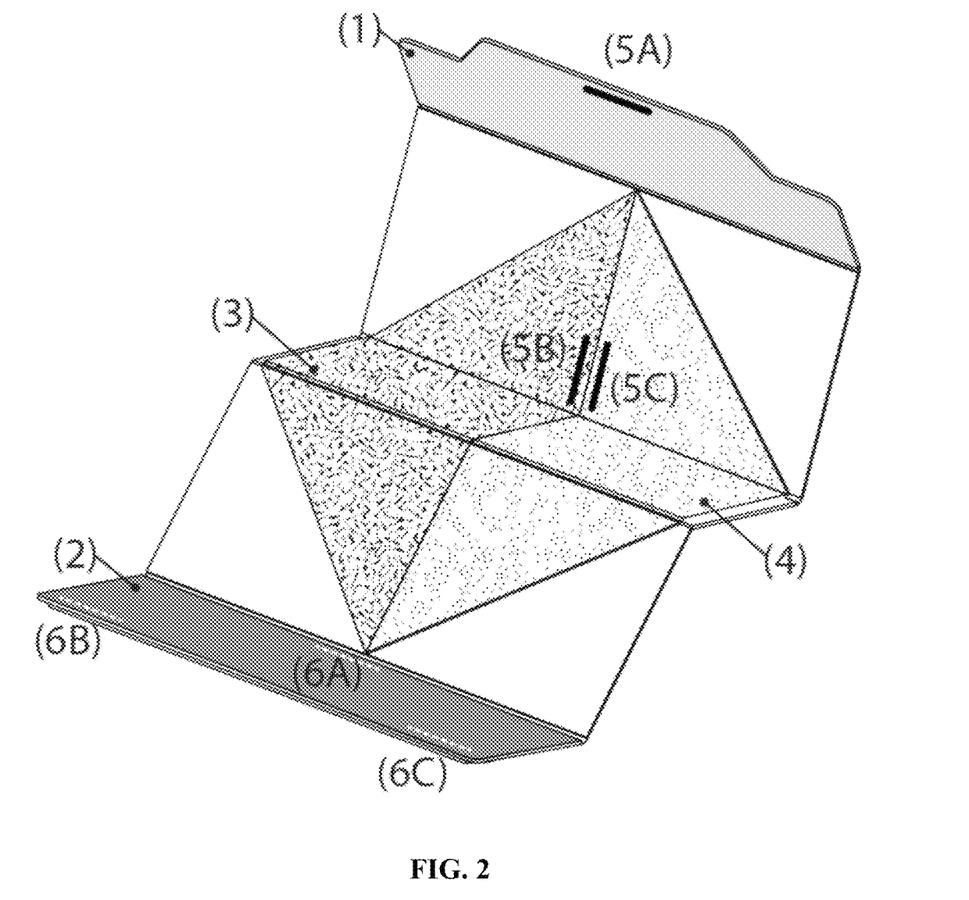
FIG. 2 depicts an isometric view of the collapsible container in the first unfolded stage of the box.

Referring to FIG. 2, when the panels 1, 2, 3, 4 are being deployed, the sensor elements 5A, 5B, 5C will not interact with interlock switch elements 6A, 6B, 6C connected to the electronic circuit board 100 integrated in the second moveable panel 2. Therefore, the electronic circuit board 100 cannot be engaged and remains OFF.

Referring to FIGS. 4-5, the container is tri-dimensionally formed but not yet fully closed. When assembling the container, the third moveable panel 3 and the fourth moveable panel 4 are pulled outward to form the inner enclosure portion (FIG. 4), and the first moveable panel 1 and the second moveable panel 2 serve as upper covers of the container (FIG. 5). In this case, the sensor elements 5A, 5B, 5C still do not interact with the interlock switch elements 6A, 6B, 6C. Therefore, the electronic circuit board 100 cannot be engaged and remains OFF.

Figure 6:
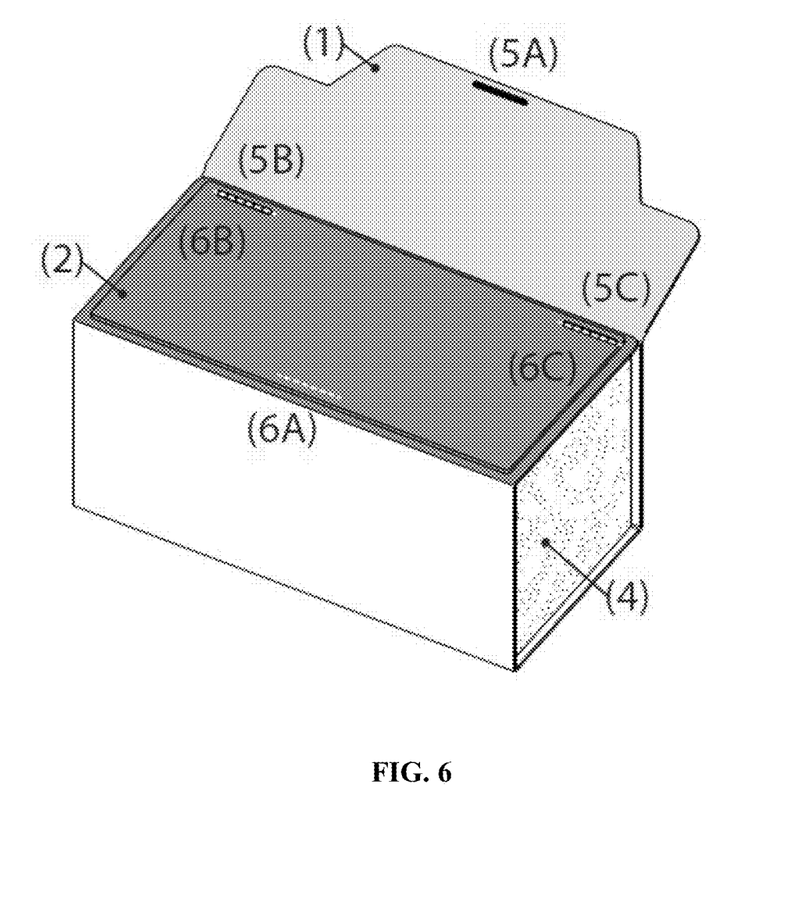
FIG. 6 depicts an isometric view of the collapsible and magnetically assemblable container formed as a box with the top opening closed but still not completely sealed.

Referring to FIG. 6, a container is created but not completely. The first moveable panel 1 and the second moveable panel 2 serve as upper covers of the container, where the first moveable panel 1 is positioned on top of the second moveable panel 2. In this case, the second sensor element 5B interacts with the interlock switch element 6B connected to the electronic circuit board 100 integrated in the second moveable panel 2, and the third sensor element 5C interacts with the interlock switch element 6C connected to the electronic circuit board 100 integrated in the second moveable panel 2. However, the first sensor element 5A does not interact with the interlock switch element 6A connected to the electronic circuit board 100 integrated in the second moveable panel 2 in this moment. Because not all the sensors are engaged, and therefore the electronic circuit board 100 cannot be engaged and remains OFF.

Figure 7:
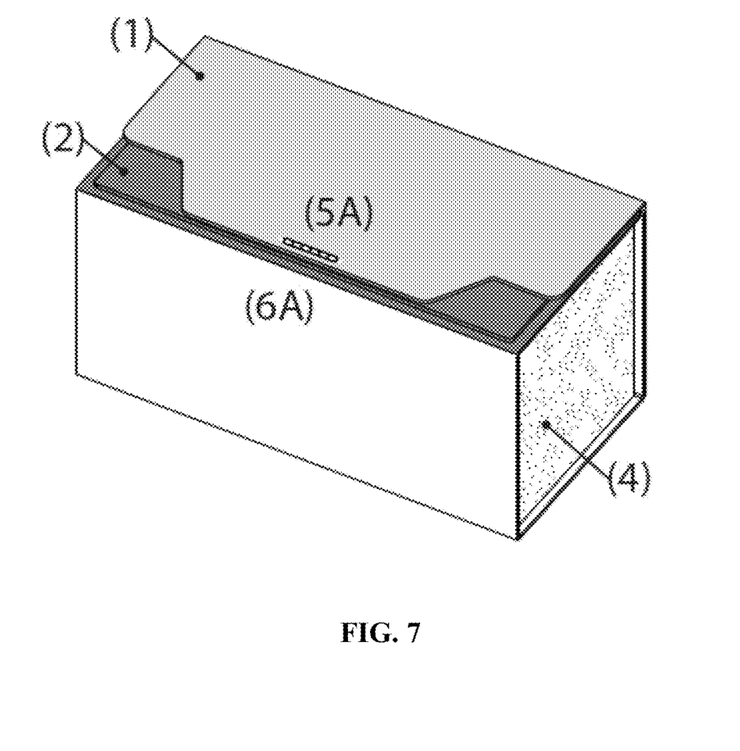
FIG. 7 depicts an isometric view of the collapsible and magnetically assemblable container formed as a box and completely sealed.

As seen in FIG. 7, which shows a fully-assembled container. In the fully-formed state, the second sensor element 5B interacts with the interlock switch element 6B, the third sensor element 5C interacts with the interlock switch element 6C, and the first sensor element 5A interacts with the interlock switch element 6A. As the collapsible container correctly forms a fully enclosed container, all the sensor elements are now engaged, and therefore the electronic circuit board can be engaged and switched ON. The one or more actuating elements can be actuated only when the container is properly assembled and closed.

In accordance to one embodiment, the one or more actuating elements, for example, including but not limited to sterilization elements such as UV LEDs, heating elements, spray elements, or laser elements. In non-sterilization applications, the actuating elements may be heating elements, optical elements, liquid applicators or any other actuating element that is operated in a closed container environment.

In accordance to one embodiment, the at least three interlock switch elements can be reed switches, magnetic-activated switches, optical sensor-activated switches, mechanical-activated switches, or temperature-activated switches.

In accordance to one embodiment, the sensor elements are closure magnets positioned on the panels, and the magnets are attracted to mating magnets on adjacent panels when the container is fully formed. These magnets may cooperate with a switch, such as a reed switch that is responsive to a magnetic field; the reed switch is one of the interlock switch elements for this embodiment, however, it is noted that other mechanical, electromechanical, or magnetic switches may also be used as an interlock to prevent activation of the actuating elements. In this embodiment, the switch includes the sensing feature as it is responsive to a magnetic field formed by the closure magnets. In this manner, the field formed by the closure magnets activates the reed switches which, in turn, activate the actuating elements such as UV sterilization elements, permitting an item placed within the container to be sterilized by the UV lights. A signal may be sent wireless by these switches to a receiver in the actuating element circuit board to permit the actuating element to be turned on.

Figure 8:
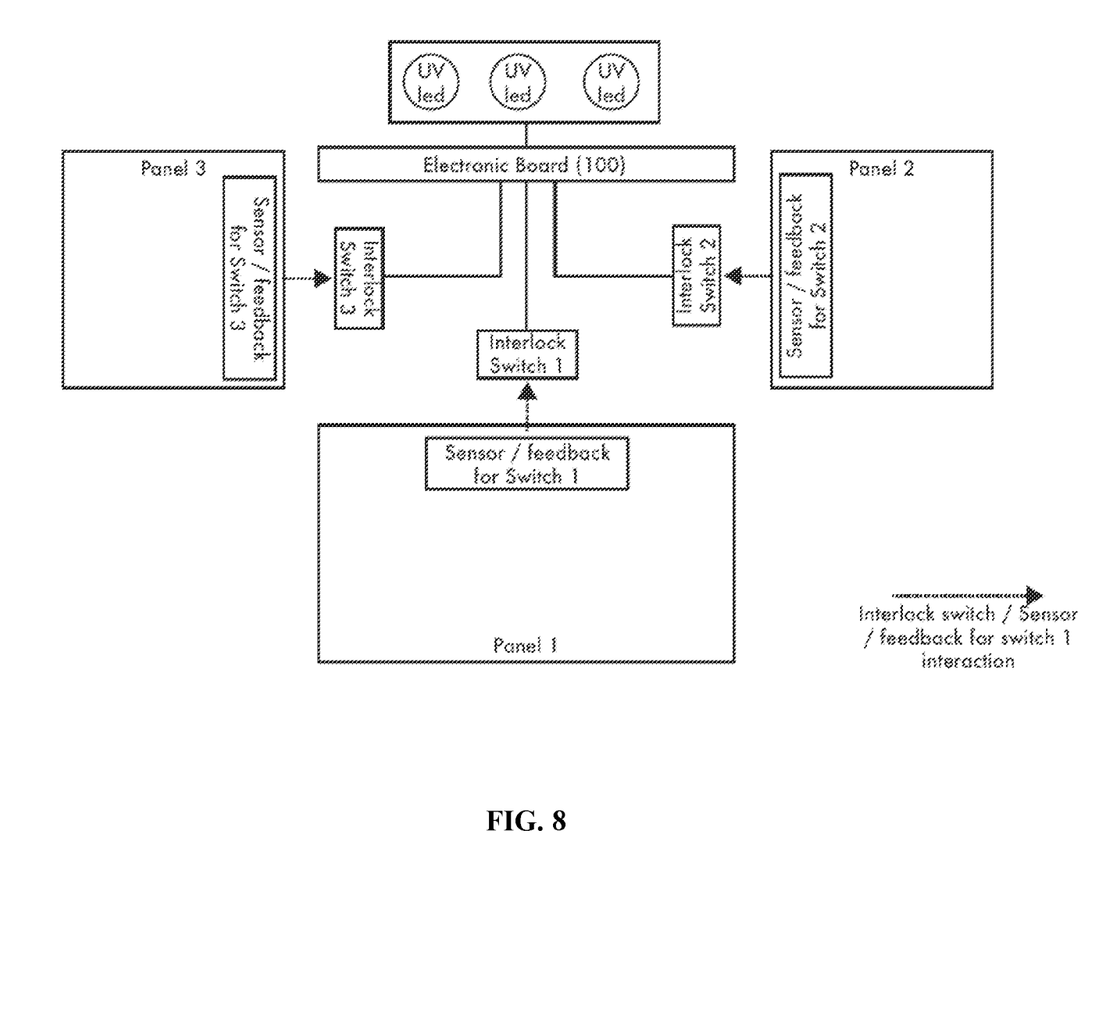
FIG. 8 depicts a functional layout of the electronic circuit board that includes the sterilization UV elements in accordance to one embodiment of the present invention.

Referring to FIG. 8. FIG. 8 shows the functional interaction among interlock switch elements for actuating one or more actuating elements. The interlock switch elements cooperate with an electronic circuit board, which has one or more actuating elements such as the UV LEDs positioned thereon or connecting therewith. In addition to the UV LEDs, the actuating elements can also be heating elements, spray elements, or laser elements or other sterilization elements or other non-sterilizing actuating elements.

In accordance to one embodiment, the interlock switch elements, for example, including but not limited to reed switches, magnetic-activated switches, optical sensor-activated switches, mechanical-activated switches, or temperature-activated switches.

In accordance to one embodiment, one or more sensor elements may optionally be positioned on the electronic circuit board or elsewhere on the container. For example, the sensor elements are magnetic sensors within the switches themselves, which can cooperate with an interlock switch to enable activation of the actuating elements such as UV LEDs. Other sensor elements may be used to determine if the container is fully assembled, such as mechanical sensors, electromechanical sensors, optical sensors, or magnetic sensors. It is noted that the one or more actuating elements are prohibited from being activated unless the collapsible container is fully and correctly assembled because the interlock or other switches prevent a user from actuating the actuating elements.

Further, the electronic circuit board may further include a power element, such as a rechargeable battery or, optionally, a connector for receiving external power, such as a USB port or Type-C port.

While the above has been described with reference to UV sterilization, it is understood that the collapsible container of the present invention may also be used for other purposes, including interlocks that prevent activation of a functional element when the container is not properly assembled. For example, in place of the sterilization elements, heating elements, spray elements, laser elements, or other actuating elements can be substituted such that the container may act as a self-contained portable heating device, coating device (e.g., spray coating such as disinfectant), or other portable functional device. In the case of elements involving heat, the foldable container sides may be made out of insulating material. In the case of spray elements, the foldable container sides may be made of waterproof materials.

In one embodiment, the foldable container sides may be made out of insulating material, including but not limited to glass fibers, silicone, polytetrafluoroethylene (PTFE), carbon fibers, aluminum and stainless steel.

In another embodiment, the foldable container sides may be made of waterproof materials, including but not limited to polytetrafluoroethylene (PTFE), glass fibers, silicone, polyurethane (PU), aluminum, stainless steel and polycarbonate.

The collapsible and assemblable container of the present invention has a dual safety mechanism of "light induction" and "magnetic induction". The sterilization is able to be performed only after the upper cover is completely closed and no light leakage is confirmed, so as to ensure that there is no UV leakage during operation.

Figure 9:
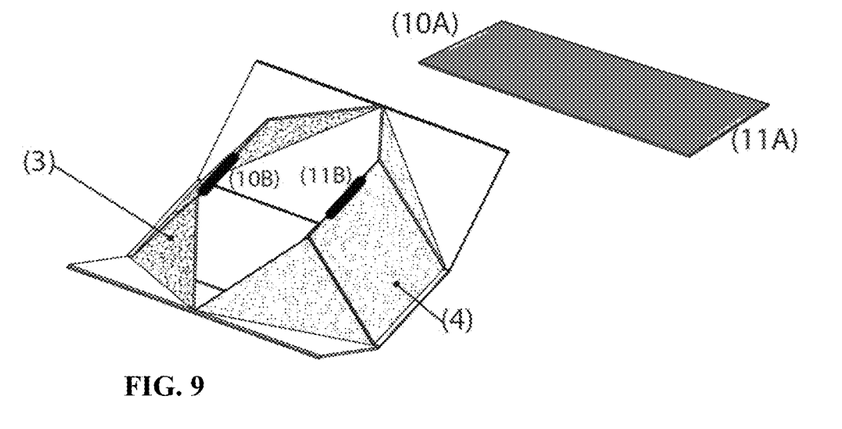
FIGS. 9, 10, and 11 depict a further embodiment of the collapsible and assemblable container with two interlock switches and a detachable cover.
Figure 10:
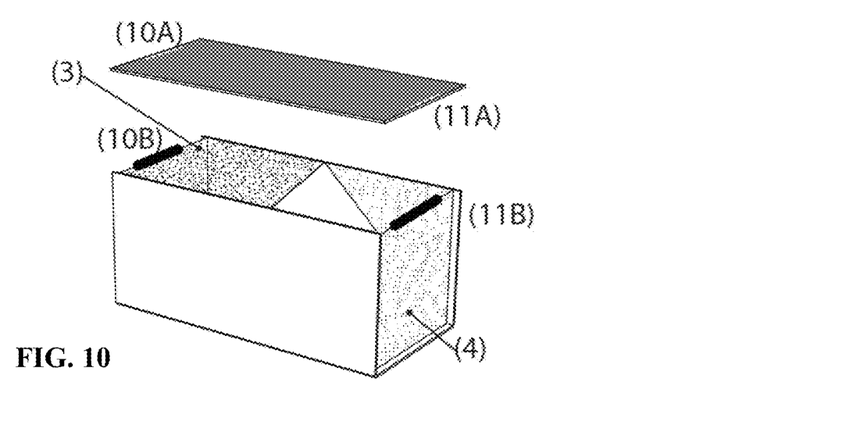
Figure 11:
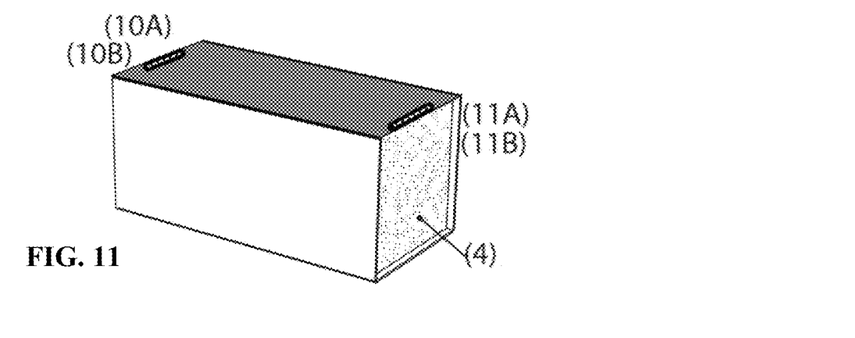

Turning to FIGS. 9-11, another embodiment of the present invention is depicted in which two interlock switches, each switch having two parts, are employed. In this embodiment, a detachable cover/lid element in provided. Although the folding container is shown with a particular folding configuration, it is understood that many other folding containers may be used to form a sterilizer apparatus according to this embodiment of the invention. That is, in this embodiment, any foldable configuration that collapses to substantially flat configuration may be used as the container portion of the sterilization apparatus.

In FIG. 9, a box element includes folding panels 3 and 4 that create a "pop-up" box configuration. In this embodiment, interlocks are provided with two parts: one part on the box, and one part on the lid. As seen in FIG. 9, one interlock includes portions 10A and 10B and one interlock includes portions 11A and 11B. As seen in FIGS. 10 and 11, each of the portions 10A and 10B and 11A and 11B are brought together only when the container is fully assembled and the lid is properly positioned. In this manner, the sterilizing elements, which may optionally be positioned on the underneath of the lid (and are thus not visible in FIGS. 9-11), may be actuated only when the interlocks are mated when the container is assembled and covered, ensuring user safety. However, each of the respective parts of a two-part interlock may be on various folded panels and not on the lid element. Note that the actuating elements of FIG. 8 may be used in this embodiment with at least one sterilization element such as a UV LED being positioned on the lid element or, optionally, on the base of the box portion.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

DEFINITIONS

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

The invention claimed is:

1. A collapsible and assemblable container, comprising:
a first moveable panel, wherein the first moveable panel includes a first sensor element;
a second moveable panel, including an electronic circuit board, the electronic circuit board comprises one or more actuating elements cooperating with at least three interlock switch elements, wherein the at least three interlock switch elements are placed on the electronic circuit board, and the at least three interlock switch elements control the one or more actuating elements;
a third moveable panel, wherein the third moveable panel includes a second sensor element; and
a fourth moveable panel, wherein the fourth moveable panel comprises a third sensor element;
wherein, during container assembly, the third moveable panel and the fourth moveable panel form an inner enclosure portion, the first moveable panel and the second moveable panel are configured as upper covers of the container, and the first moveable panel is positioned on top of the second moveable panel,
and wherein the second sensor element of the third moveable panel interacts with a first of the at least three interlock switch elements, and the third sensor element of the fourth moveable panel interacts with a second of the at least three interlock switch elements,
if the first sensor element of the first moveable panel does not interact with one or more of the at least three interlock switch elements, the electronic circuit board remains OFF;
else if the first sensor element of the first moveable panel interacts with each of the at least three interlock switch elements, the one or more actuating elements are actuated.

2. The collapsible and assemblable container of claim 1, wherein the one or more actuating elements comprise sterilization elements, heating elements, spray elements, or laser elements.

3. The collapsible and assemblable container of claim 2, wherein the sterilization elements comprise at least three of UV LEDs.

4. The collapsible and assemblable container of claim 1, wherein the at least three interlock switch elements comprise reed switches, magnetic-activated switches, optical sensor-activated switches, mechanical-activated switches, or temperature-activated switches.

5. The collapsible and assemblable container of claim 1, wherein the electronic circuit board further comprises a power element comprising a rechargeable battery and a connector.

6. The collapsible and assemblable container of claim 5, wherein the connector comprises a USB port or a Type-C port.

7. The collapsible and assemblable container of claim 1, wherein all panels are made from insulating materials or waterproof materials.

8. The collapsible and assemblable container of claim 1, wherein the insulating materials comprise one or more of glass fibers, silicone, polytetrafluoroethylene (PTFE), carbon fibers, aluminum and stainless steel.

9. The collapsible and assemblable container of claim 1, wherein the waterproof materials comprise one or more of polytetrafluoroethylene (PTFE), glass fibers, silicone, polyurethane (PU), aluminum, stainless steel and polycarbonate.

10. The collapsible and assemblable container of claim 1, wherein the sensor elements are magnets, and the magnets are attracted to mating magnets on adjacent panels when the container is fully formed.

11. The collapsible and assemblable container of claim 1, wherein the electronic circuit board further comprises one or more sensors that prohibit the one or more actuating elements from being activated unless the collapsible container is fully and correctly deployed.

12. The collapsible and assemblable container of claim 1, wherein the first and second panels are connected by plural intermediate panels.

13. The collapsible and assemblable container of claim 12, wherein the third and fourth panels are positioned over the plural intermediate panels.

14. The collapsible and assemblable container of claim 13, wherein the plural intermediate panels form an outer enclosure portion surrounding the inner enclosure portion formed by the third and fourth panels.

15. A collapsible and assemblable sterilizing container, comprising:
   an electronic circuit board, the electronic circuit board including one or more sterilizer elements positioned thereon cooperating with at least two interlock switches, where the at least two interlock switch elements control the one or more sterilizer elements;
   a collapsible and assemblable container having a plurality of folding panels and/or detachable panels, the electronic circuit board being mounted on one of the folding panels or on one of the detachable panels;
   at least a portion of each of the at least two interlock switches respectively positioned on different folding panels such that the interlock switches are open when the container is in a collapsed state and the interlock switches are closed with the container is in an assembled state;
   when at least one of the at least two interlocks s in an open state, the sterilizer elements cannot be operated;
   when all of the interlock switches are in closed state, the container is fully assembled and the sterilizer elements can be operated.

16. The collapsible and assemblable sterilizing container of claim 15, wherein the sterilizer elements are light emitting elements.

17. The collapsible and assemblable sterilizing container of claim 16, wherein the light emitting elements are light emitting diodes.

18. The collapsible and assemblable sterilizing container of claim 17, wherein the light emitting diodes are ultraviolet light emitting diodes.

* * * * *